United States Patent [19]

Morrow et al.

[11] 4,161,066

[45] Jul. 17, 1979

[54] ORTHODONTIC BRACKET

[76] Inventors: Jim B. Morrow, 10701 Meath Dr., St. Louis County, Mo. 63123; Peter G. Sotiropoulos, 100 S. Fairway Dr., Belleville, Ill. 62223

[21] Appl. No.: 808,189

[22] Filed: Jun. 20, 1977

[51] Int. Cl.² ............................................. A61C 7/00
[52] U.S. Cl. .................................................. 32/14 A
[58] Field of Search ...................................... 32/14 A

[56] References Cited

U.S. PATENT DOCUMENTS

| | | | |
|---|---|---|---|
| 1,369,665 | 2/1921 | Johnson | 32/14 A |
| 3,421,221 | 1/1969 | Silverman et al. | 32/14 A |
| 3,461,559 | 8/1969 | Silverman et al. | 32/14 A |
| 3,464,113 | 9/1969 | Silverman et al. | 32/14 A |
| 3,946,488 | 3/1976 | Miller et al. | 32/14 A |

Primary Examiner—Russell R. Kinsey
Assistant Examiner—John J. Wilson
Attorney, Agent, or Firm—Gravely, Lieder & Woodruff

[57] ABSTRACT

An orthodontic bracket includes a base which is capable of being attached to a band that surrounds a tooth or directly to the tooth itself, and the base contains ways along which at least one insert slides. Pins fit through the base to maintain the insert in a fixed position thereon. The insert has an outwardly opening slot which receives an arch wire that extends along the row of teeth in which the tooth is located, and the arch wire is attached to the insert by small tie wires. By moving the insert relative to the base, it is possible to change the orientation of the force exerted on the tooth by the arch wire. Moreover, the bracket normally has two inserts which slide independently of each other on the base until fixed in position by the pins, and this enables the bracket to be easily converted from one configuration to another. For example, the bracket is easily changed from a large single bracket to a medium twin or to a wide twin and vice-versa.

17 Claims, 8 Drawing Figures

ORTHODONTIC BRACKET

BACKGROUND OF THE INVENTION

This invention relates in general to orthodontic appliances and more particularly to orthodontic brackets.

In orthodontics it is common practice to reposition a malpositioned tooth by applying a force to that tooth through an arch wire which generally follows the arch defined by the row of teeth in which the malpositioned tooth is located. The arch wire is normally connected with the teeth by bands which fit around the individual teeth and brackets which are secured to the bands and engaged with the arch wire. The correctly positioned teeth merely serve as anchors for the arch wire which exerts forces on the malpositioned teeth to move those teeth into correct positions.

As to each malpositioned tooth, the shape of the bracket for that tooth, its location on the band around the tooth, and the configuration of the arch wire at the bracket are all critical to repositioning the tooth. As a consequence, the brackets are supplied in many different configurations. For example, the basic configuration is referred to as a "single" which is merely a relatively narrow projection from the band. Next, is a "double" which like the single is a single projection from the band, only it is about twice as wide as the single. Then there are "narrow twin," "medium twin," and "wide twin" brackets, each of which has two projections from a common base that is secured to a band. The spacing between the projections is less for the narrow twin than for the wide twin as the names imply.

The wide variety of brackets needed for orthodontic work requires the orthodontist to maintain a large supply of such brackets. Moreover, orthodontic treatment relies on gradual migration of teeth to their proper positions upon the application of correctly oriented forces, and by its very nature requires repeated visits to the orthodontist at closely spaced intervals, often as short as a week or two. These visits give the orthodontist an opportunity to inspect the migration of the malpositioned teeth and to further make adjustments in the orthodontic appliances. These adjustments often involve converting from one configuration of bracket to another or changing the position of a bracket on its band. This requires complete removal of the band from the tooth so that the new or repositioned bracket can be welded to the band at the proper location.

SUMMARY OF THE INVENTION

One of the principal objects of the present invention is to provide a single orthodontic bracket which serves the function of a wide variety of conventional brackets. Another object is to provide an orthodontic bracket which is adjustable to assume a wide variety of bracket configurations. A further object is to provide a bracket of the type stated which may be moved relative to its band so that it can, in effect, be repositioned on its band without welding or removal of the band from the tooth. An additional object is to provide a bracket of the type stated which is easily adjusted on the patient's tooth. These and other objects and advantages will become apparent hereinafter.

The present invention is embodied in an orthodontic bracket that includes a base capable of being attached to an orthodontic band or directly to a tooth and an insert which is initially movable with respect to the base and is configured to engage an arch wire. The invention also consists in the parts and in the arrangements and combinations of parts hereinafter described and claimed.

DESCRIPTION OF THE DRAWINGS

In the accompanying drawings, which form part of the specification and wherein like numerals and letters refer to like parts wherever they occur.

DETAILED DESCRIPTION

Figure 1:
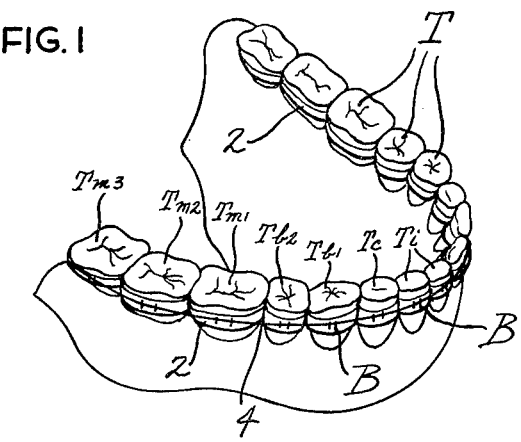
FIG. 1 is a perspective view of a lower jaw fitted with orthodontic appliances, including brackets of the present invention.

Referring now to the drawings (FIG. 1), B designates an adjustable orthodontic bracket which is attached to a band 2 that encircles the crown of a tooth T. The tooth T is one of a number of teeth T in a row, and generally speaking each tooth in the row is surrounded by a different band 2, and each band has a bracket B or some other type of wire-retaining device attached to it. By means of the brackets B or other devices an arch wire 4 is connected to all the teeth of the row, and this wire follows the arch of the row. If a tooth T within the row is malpositioned, the arch wire 4 is utilized to exert a force on the tooth T so as to urge it to the proper location within the row. This force is applied through the bracket B and the band 2 for the particular tooth T. The bands 2 and brackets B on the correctly positioned teeth T of the row serve as anchors for the arch wire 4.

Figure 2:
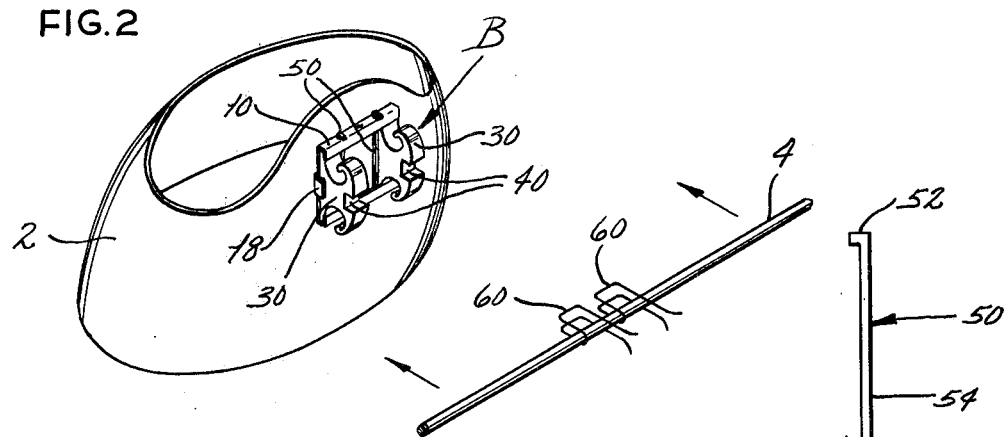
FIG. 2 is a perspective view of a band provided with the bracket of the present invention.

The band 2 (FIG. 2) for each tooth T is conventional, it normally being formed from stainless steel. The band 2 fits around the crown of the tooth T and is secured firmly thereto by a suitable cement. The bracket B is attached to the outside surface of the band 2, preferably by welding.

Figure 3:
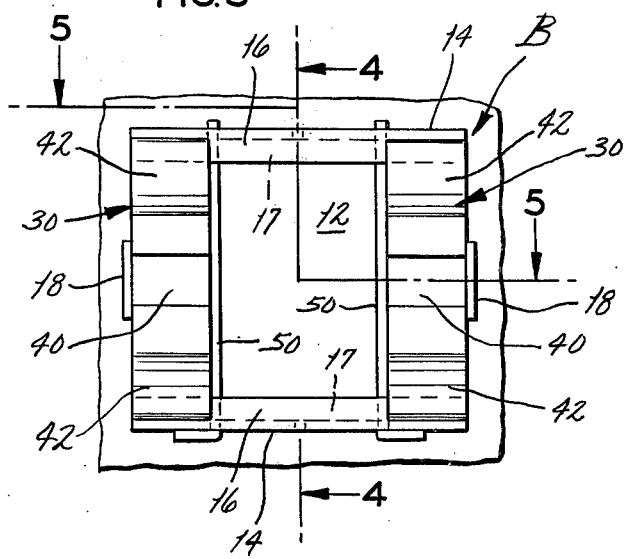
FIG. 3 is a front elevational view of the bracket with its inserts in the wide twin configuration.

The bracket 2 includes (FIGS. 2-5) a base 10 having a back wall 12 which along its upper and lower edges merges into edge walls 14 which in turn merge into inwardly directed flanges 16. The flanges 16 overlie the back wall 12, and form channel-like ways 17 (FIG. 4) on the base 10. Since the flanges 16 are not very deep, a substantial portion of the back wall 12 is exposed between the inner edges of the two flanges 16 (FIG. 3). The edge walls 14 are relatively narrow, and as a consequence, the channel-like ways 17 are likewise quite narrow, normally measuring about 0.007 inches in width. The base 10 is tack welded to the band 2 along its back wall 12, and may be flat or curved, depending on the type of tooth T with which it is used. For example, when used on a band 2 for a flat or wide tooth, such as an incisor or molar, the base 10 will be flat. On the other hand, when used with a band 2 for a narrow tooth, such as a cuspid or bicuspid, the back wall is curved to generally follow the contour of the tooth T. Generally speaking, the base 10 is about 6 mm in length and about 3 mm high.

At each end of the back wall 12 is a forwardly projecting stop 18 (FIGS. 3 and 5), which may be an extended portion of the back wall 12 that has been turned forwardly. Each edge wall 14 has three locking apertures 20 (FIGS. 4 and 5) which are spaced at equal intervals from one another and from the end stop 18. In other words, the distance between either end stop 18 and the closest apertures 20 equals the spacing between the center aperture 20 and the aperture 20 on either side of it. Thus, the apertures 20 in the upper edge wall 14 align with the apertures 20 in the lower edge wall 14. Preferably, the apertures 20 are rectangular in configuration.

Aside from the base 10, each bracket B further includes at least one insert 30. Normally, it has two inserts 30. Each insert 30 is formed from a suitable metal such as stainless steel and has a pedestal 32 (FIG. 4) which fits into the space between the two flanges 16 on base 10. Indeed, the insert 30 has upper and lower guide surfaces 34 which are located opposite the opposed inwardly presented edges of the flanges 16. Projecting outwardly from the guide surfaces 34 are retaining lips 36 which fit behind the flanges 16 on the base 10 so as to be engaged with the ways 17. The retaining lips 36 are narrower than the spacing between the flanges 16 and the back wall 12 of the base 10, and a limited amount of clearance exists between the edges of those flanges 16 and the guide surfaces 34 so that the inserts 30, unless otherwise confined, slide easily in the ways 17 of the base 10 from one end stop 18 to the other. Nevertheless, the clearance between the edges of the flanges 16 and the guide surfaces 34 is not so great so as to enable the insert 30 to be rotated with ease and then withdrawn from the space between the two flanges 16. The width of the insert 30 is slightly less than the spacing between the apertures 20 in the edge walls 14 of the base 10.

The pedestal 34 of each insert 30 merges into a forward portion or crown 38 (FIG. 4) having a forwardly opening slot 40 which is capable of receiving the arch wire 4. The slot 40 is preferably rectilinear in configuration, it having parallel side walls and a base wall with the former being generally horizontal and the latter being parallel to the back wall 12 of the base 10. Both above and below the slot 40, the crown 38 has tie wings 42, which curve rearwardly toward the retaining lips 36. The tie wings 42 are separated from the pedestal 32 by undercuts 44 having curved surface areas.

Figure 4:
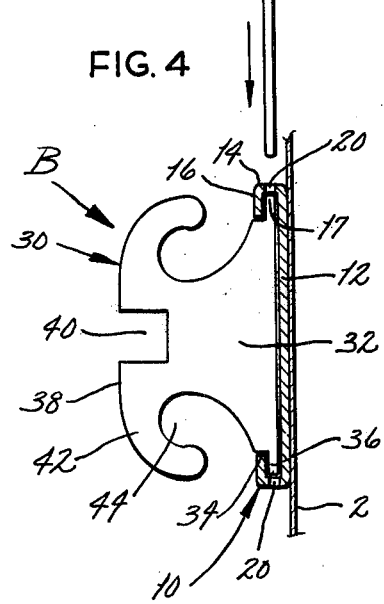
FIG. 4 is a sectional view taken along line 4—4 of FIG. 3 and showing the locking pin removed from the base.
Figure 5:
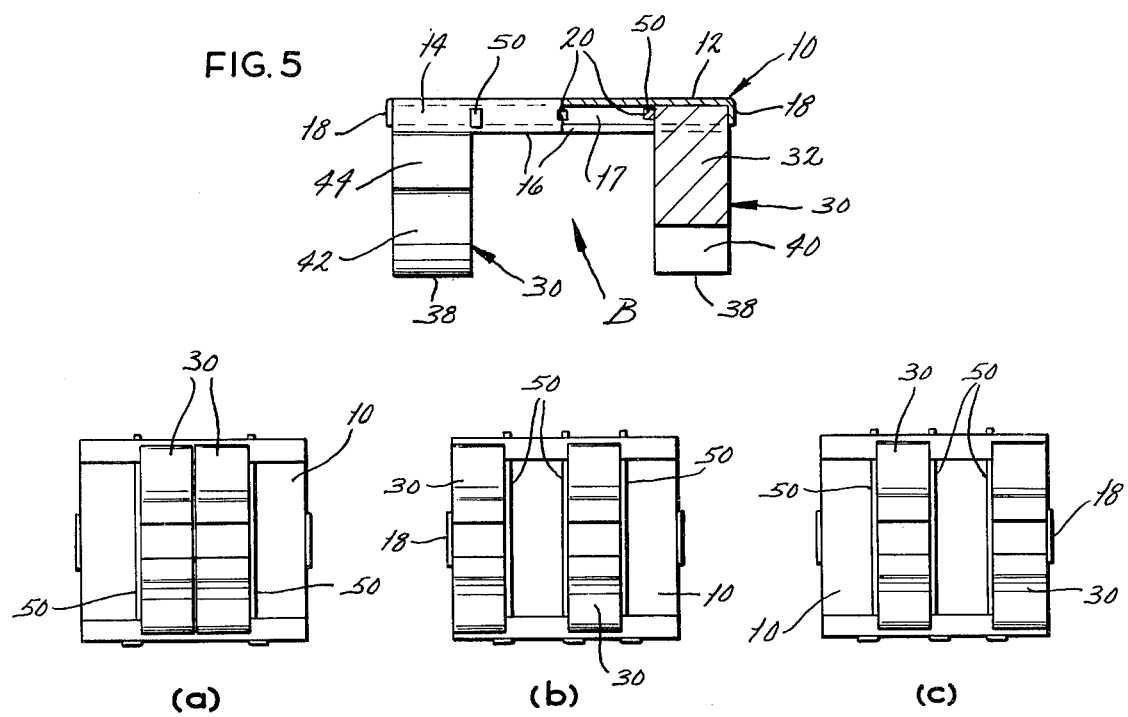
FIG. 5 is a partial top and sectional view of the bracket taken along line 5—5 of FIG. 3.

In addition to the base 10 and the inserts 30, each bracket B is further provided with locking pins 50 (FIGS. 2-5) which fit through the sets of aligned apertures 20 in the edge walls 14 of the base 10 and prevent the inserts 30 from moving on the base 10. Each pin 50 has a head 52, which is larger than the apertures 20 in the base 10, and a shank 54 extended from the head 52 (FIG. 4). The shank 54 is longer than the height of the base 10 and is square in cross section, but slightly smaller than the apertures 20 so as to be capable of being received in the apertures 20. When the shank 54 of a pin 50 is inserted through aligned apertures 20, it forms an obstruction between the two edge walls 14, and this obstruction lies to the side of the pedestal 32 on the insert 30, so that the insert 30 will not move past the pin 50. The heads 54 of the pins 50 prevent the pins 54 from falling completely through the apertures 20 in the base 10. To prevent the pins 50 from rising out of the apertures 20, the lower ends of the pins 50 are bent over along the lower edge wall 14. Thus, a single insert 30 may be captured between a pair of pins 50 located in adjacent sets of apertures 20 or between an end stop 18 and a pin located in the set of apertures 20 immediately beyond that end stop 18.

Normally, the bracket B is supplied with two inserts 30 and a common base 10. The locking pins 50 are readily available inasmuch as they are used with other orthodontic appliances. The bracket B, however, may be supplied with a single insert.

OPERATION

The bracket B enables the orthodontist to, in effect, construct from a single bracket B, brackets suitable for a wide variety of correctional procedures. This is achieved by placing the inserts 30 at desired locations on the base 10. For example, where two inserts 30 are on a common base 10, the orthodontist may construct a double bracket (FIG. 6a) by moving the two inserts 30 together at the center of the base and then inserting locking pins 50 through the aligned apertures 20 located adjacent to the exposed sides of the pair of inserts 30. This prevents the inserts 30 from moving in either direction along the base 10, and the two inserts 30 in combination produce the equivalent of a double bracket. On the other hand, where a wide twin (FIG. 6d) is desired, the orthodontist moves the two inserts 30 apart to bring the left insert 30 against the left end stop 18 and the right insert 30 against the right end stop 18, whereupon locking pins 50 are inserted through the sets of aligned apertures 20 located immediately inwardly from the end stops 18. This confines the two inserts 30 to end positions against the end stops 18, and in that position the pins 50 prevent the inserts 30 from moving inwardly toward each other. To construct a narrow twin (FIGS. 6b & 6c) one of the inserts 30 is located against an end stop 18 and held in that position with a locking pin 50, while the other insert 30 is positioned between a center set of apertures 20 and the set of apertures 20 located immediately beyond the centermost set. Moreover, in the case of the double configuration and narrow twin configurations, it is possible to change the location of the inserts on the base and still retain the same configuration. For example, the orthodontist may provide a double in which the two inserts are located between one of the end stops 18 and a pin extended through the center set of apertures 20 (FIGS. 6e and 6f). Even greater variations as to location are available when a single insert 30 is utilized. Furthermore, the change in configuration or location may be made during treatment, that is, after the bands 2 have been installed on the teeth T and after the brackets B have been welded to the bands 2.

The orthodontic treatment of a patient commences with an examination, at which time X-ray photographs of teeth and jaws are taken. Also an impression of the teeth is made and converted into a cast showing the teeth as they existed prior to treatment. From the examination, the X-ray photographs, and the cast, the orthodontist develops a plan for treatment.

Usually the plan for treatment calls for so-called braces, and consequently, the orthodontist must select a specific bracket B for each tooth as well as the angle at which that bracket B is applied to its band 2. Either the orthodontist tack welds the brackets B to the bands 2 or the manufacture of the bands 2 supplies them with the brackets B already affixed. In either case, a tack weld is made between the band 2 and the base 10 of the bracket B. In this regard, the inserts 30 are easily shifted on the base 30 so as to not interfere with the welding head of the tack welding machine. Then the inserts 30 of each bracket B are arranged on their bases 10 to produce the desired configuration, and that configuration is retained by inserting lock pins 50 through the appropriate sets of apertures 20 in the base 10. The protruding ends of the pins 50 are bent over along the lower edge wall 14 to secure the pins 50 firmly in place.

Once the brackets B are attached to their respective bands 2 and adjusted to the desired configuration, the orthodontist fits the bands 2 over the teeth such that the brackets B project outwardly (FIG. 1). Consequently, the slots 40 in the inserts 30 open outwardly toward the patient's lips and cheeks. Next, the orthodontist places an arch wire 4 through the slots 40 in all the brackets B and secures the arch wire 4 to the inserts 30 for the brackets B, there being a single arch wire 4 for each row of teeth T. The attachment is effected in the usual manner, that is, by passing the midportion of a tie wire 60 (FIG. 2) over the arch wire 4 in a direction transverse to the arch wire 4 and then extending the tie wire 60 behind the tie wings 42 on the insert 30 in a direction generally parallel to the arch wire 4. In this regard, the wire 60 extends through the undercuts 44 located behind the two tie wings 42. Then the ends of the tie wire 60 are brought forwardly at the opposite side of the insert 30 and are twisted together over the arch wire 4 so that the midportion of the tie wire 60 is at one end of slot 40, while the twisted ends are at the other end of the slot 40. The selection for the configuration of the bracket B, its location on the bands 2, and the nature and configuration of the arch wire 4 all influence the magnitude and orientation of a force applied to any tooth T. These selections are the subject matter of orthodontics in general and will not be considered in detail.

Figure 6:
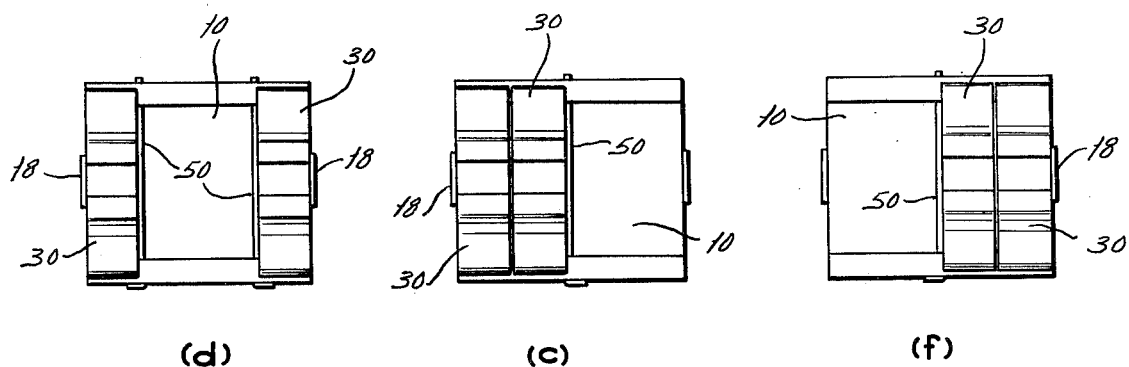
FIG. 6 is a plurality of front elevational views showing the various configurations to which the inserts may be moved, including double (a), medium twin (b and c), wide twin (d), double left (e), and double right (f)

One major advantage of the bracket B is that a single bracket B will assume a variety of different configurations (FIG. 6). Thus, the orthodontist need not maintain a large supply of different brackets on hand.

Another advantage is that the configuration of the bracket B is easily altered while the bracket B is affixed to its band 2 and the band is around the tooth T. For example, a bracket is easily converted from a double to a wide twin or vice-versa. The change is achieved by withdrawing the locking pins 50 from the base 10 and then shifting the inserts 30 to positions for the altered configuration. New locking pins 50 are installed to retain the inserts 30 in their new positions.

Figure 7:
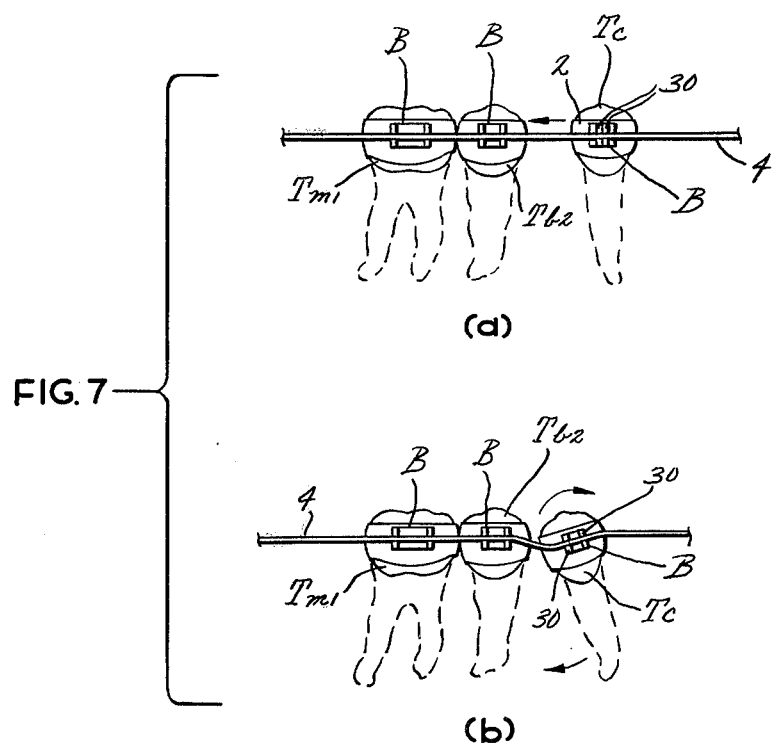
FIG. 7 is a side elevational view of teeth in the lower jaw showing the movement of a cuspid into a space vacated by the extraction of a first bicuspid.

The ability to change configuration is useful in repositioning teeth after an extraction is made for the purpose of alleviating overcrowding (FIG. 7). For example, the first cuspids $T_{b1}$ may be extracted because the incisors $T_1$ and cuspids $T_c$ located between them are crowded to the extent that they do not form a uniform continuation of the row, but instead tend to overlap. Once the first bicuspid $T_{b1}$ is removed, the cuspids $T_c$ and second bicuspid $T_{b2}$ will migrate into the void left by the first bicuspids $T_{b1}$, but the process is indeed slow and a good chance exists that these teeth will assume improper angles. Moreover, the teeth in the opposite row may be adversely affected as a result of the void left by the extraction, unless the void is occupied as soon as possible.

The foregoing problems resulting from the extraction of the first bicuspids $T_{c1}$ are overcome by urging the cuspids $T_c$ and second bicuspids $T_{b2}$ into the void through proper orthodontic procedures. This involves fitting bands 2 around the remaining teeth T in the row in the usual manner. The bands 2 on the second bicuspid $T_{b2}$ and first molar $T_{m1}$ are provided with brackets B which have been adjusted for the wide twin configuration, while the brackets B on the cuspid $T_c$ are provided in the double configuration (FIG. 7a). Moreover, the arch wire 4 is arranged such that it urges the cuspid $T_c$ toward the second bicuspid $T_{b2}$. In this regard, the molars $T_m$ and second bicuspid $T_{b2}$ serve as an anchor for the wire and most of the movement occurs at the cuspid $T_c$. The cuspid $T_c$ does not move into the void in a uniform manner, but instead tends to tilt into the void with the crown experiencing most of the movement and the tip of the root being more or less fixed in the jawbone.

To bring the tooth $T_c$ back into a vertical disposition, a torque is applied to it through the arch wire and this torque is oriented such that the root of the tooth $T_c$ is urged toward the root of the second bicuspid $T_{b2}$. To impart the torque, the bracket B on the cuspid is converted from a double configuration to a wide twin configuration (FIG. 6b). Hence, immediately beyond the second bicuspid $T_{b2}$ the arch wire 4 loops downwardly and extends through the rear insert 30 on the bracket B for the cuspid $T_c$. It continues through the front insert 30 and then passes on to the bracket B of the latteral incisor $T_1$. As a consequence, the first insert 30 is urged upwardly while the second may be urged downwardly, and this of course creates the torque about a generally horizontal axis extended transversely of the row of teeth T. The torque moves the root into a more vertical disposition. Once the root has acquired a vertical disposition, the bracket B on the cuspid is moved back to a double configuration and the procedure is repeated for as many times as is necessary to work the cuspid $T_c$ into the void.

Figure 8:
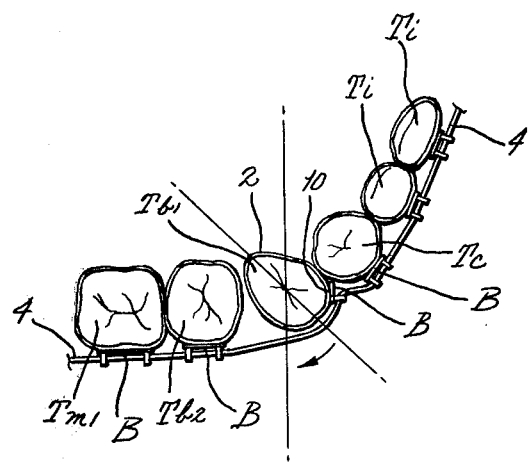
FIG. 8 is a partial plan view of the lower jaw showing rotation of a first bicuspid about its vertical axis to bring the tooth to proper position of rotation.

The ability to change the location of the insert 30 relative to the base 10 greatly facilitates the rotation of a tooth. For example, if a first bicuspid $T_{b1}$ is rotated counterclockwise from the angular position it should properly assume, a torque must be applied to the tooth $T_{b1}$ about its vertical axis in the clockwise direction (FIG. 8). This is achieved by again fitting bands 2 around the teeth T in the row and connecting an arch wire 4 to the bands 2. The rotated tooth $T_{b1}$ is likewise fitted with a band 2 and the base 10 of the bracket B on that band 2 is moved as close to the adjacent cuspid $T_c$ as possible. Indeed, it may even be possible to fit the base 10 between the rotated bicuspid $T_{b1}$ and the cuspid $T_c$. When the base 10 is so disposed, the opposite end of the base 10 should be located slightly inwardly from the arch wire 4 which is thereupon connected to an insert 30 on the bracket B so that the arch wire 4 tends to apply a torque about the vertical axis of the tooth $T_{b1}$. The tooth $T_{b1}$ will rotate, and as it does, the insert 30 will move outwardly along with the connected portion of the arch wire 4 so that the wire 4 becomes less effective. The effectiveness of the arch wire 4 is restored, however, by moving the insert 30 of the partially rotated tooth $T_{b1}$ inwardly or back toward the cuspid $T_c$. Indeed, the insert 30 is moved incrementally until the tooth $T_{b1}$ assumes its correct position.

While the brackets B as heretofore described are attached at their bases 10 to the bands 2 which encircle the teeth, it is possible to attach the bases 10 of the brackets B directly to the teeth using direct bonding procedures which are well established in the science of orthodontics. Also, the ways 17 into which the retaining lips 34 of the inserts 30 project, need not be opposed channels but instead may be any configuration suitable for preventing outward withdrawal while permitting lateral sliding. Finally, locks other than the pins 50 may be used to secure the inserts 30 against sliding.

This invention is intended to cover all changes and modifications of the example of the invention herein chosen for purposes of the disclosure which do not constitute departures from the spirit and scope of the invention.

What is claimed is:

1. In combination with an arch wire which is adapted to extend along a row of teeth, an improved orthodontic bracket for connecting the tooth with the arch wire, said bracket comprising: a base attached firmly to the tooth or to a band that fits around the tooth, the base having at least one slide way extended along it, two inserts mounted on the base and being engaged with the slide way such that they are capable of sliding along the way independently of each other, but cannot be withdrawn outwardly from the base, each insert having an outwardly opening slot which receives the arch wire, and means for securing the inserts in any one of a plurality of positions along the slide way of the base, whereby the configuration of the bracket may be altered so as to enable the bracket to perform different orthodontic functions.

2. In combination with an arch wire which is adapted to extend along a row of teeth, an improved orthodontic bracket for connecting the tooth with the arch wire, said bracket comprising: a base attached to the tooth or to a band that fits around the tooth, the base having at least one slide way that extends along it in a generally horizontal direction; at least one insert engaged with the slide way and being configured such that it is free to slide horizontally along the way, but cannot be withdrawn outwardly from the way or moved vertically with respect to the way, the insert further having an outwardly presented portion that is configured to receive the arch wire extended along the row of teeth, and securing means for fastening the insert to the base in any one of a plurality of fixed positions to which it may be moved along the slide way, said means providing a positive stop to movement of the insert in either direction horizontally along the way.

3. The combination according to claim 2 wherein the base further includes end stops which block movement of the insert at both ends of the horizontal ways so that the insert will not slide off either end of the way, each end stop constituting a portion of the means for securing the insert when the insert is at the end of the base at which said stop is located.

4. The combination according to claim 2 wherein the base has a pair of ways which form channels thereon, and the insert has lips which project into the ways such that the insert is free to slide horizontally along the base.

5. The combination according to claim 4 wherein the channels formed by the ways open toward each other.

6. The combination according to claim 2 wherein the insert has an outwardly opening horizontal slot sized to receive the arch wire.

7. The combination according to claim 6 wherein the insert has a tie wing projecting laterally therefrom on each side of the slot so that a tie wire may be secured to the insert to hold the ach wire in the slot.

8. The combination according to claim 2 wherein the securing means comprises at least one pin extended through the base, the pin being removable from the base to permit movement of the insert along the way.

9. The combination according to claim 2 wherein the pin extends through the way and along the side of the insert.

10. The combination according to claim 2 wherein the insert is one of two inserts and the securing means holds both inserts in any one of a plurality of fixed positions to which those inserts are moved on the base.

11. The combination according to claim 2 wherein the base of the bracket has a back wall, edge walls extended forwardly from the back wall along the upper and lower margins thereof, and a flange on each of the edge walls, with the flanges being projected toward each other and further being spaced outwardly from the back wall to form the slide ways; and wherein the insert of the bracket has a pedestal that fits between the two flanges on the base and lips that project loosely into the ways and enable the insert to slide along the base.

12. The combination according to claim 11 wherein the means for securing the insert includes at least one pin that extends through both of the edge walls and blocks movement of the insert along the base.

13. The combination according to claim 12 wherein the bracket further comprises end stops attached to the back wall at each end thereof and projected forwardly therefrom intermediate the ends of the ways to prevent the inserts from moving out of the ends of the ways, each end stop further serving as part of the securing means when an insert is in a fixed position against it.

14. An orthodontic bracket for connecting an arch wire that extends along a row of teeth to a tooth in that row, said bracket comprising: a base suitable for being attached directly to the tooth or to a band surrounding the tooth; the base having a back wall and generally horizontal edge walls projected forwardly from the upper and lower margins of the back wall, the edge walls having a plurality of apertures therein with the apertures in those walls being aligned generally vertically in pairs, the base further having flanges projected from the edge walls with the flanges overlying the back wall, yet being spaced forwardly from the back wall, the flanges having parallel free margins which are generally horizontal; an insert mounted on the base and having a pedestal that projects away from the back wall of the base and lips that project from the pedestal and into the spaces between the flanges and the back wall such that the insert, unless otherwise obstructed, can move horizontally along the base to a plurality of positions but cannot be withdrawn outwardly from the base or moved vertically with respect to the base, the insert further having a forward portion on the pedestal with the forward portion being configured to receive an arch wire; and at least one pin extended through a pair of apertures in the edge walls to the side of the insert so as to interfere with movement of the insert along the base and thereby contribute to the securement of the insert in a fixed position on the base.

15. An orthodontic bracket according to claim 14 wherein the base further has end stops projected forwardly from the ends of the back wall sufficiently to interfere with the insert and prevent it from sliding out of the ends of the base.

16. An orthodontic device according to claim 14 wherein another pin passes through another pair of aligned apertures and extends along the other side of the insert such that the insert is captured between the two pins.

17. An orthodontic bracket according to claim 14 wherein the insert is one of two inserts mounted on the base between the edge walls and flanges, the inserts when unsecured being capable of moving independently of each other.

* * * * *